United States Patent [19]

Arnold

[11] 4,340,667
[45] Jul. 20, 1982

[54] RAPID, SEMI-AUTOMATED METHOD FOR DETERMINING DIBUCAINE NUMBERS

[75] Inventor: William P. Arnold, Charlottesville, Va.

[73] Assignee: The University of Virginia, Charlottesville, Va.

[21] Appl. No.: 151,602

[22] Filed: May 20, 1980

[51] Int. Cl.$^3$ ............................................. C12Q 1/46
[52] U.S. Cl. ..................................... 435/20; 435/810; 23/230 B; 252/408; 424/2; 424/7
[58] Field of Search ................. 435/20, 291, 184, 810, 435/805; 424/2, 7; 23/230 B; 252/408 R

[56] References Cited

U.S. PATENT DOCUMENTS 3,401,086  9/1968  Hoffmann et al. ................... 435/20

OTHER PUBLICATIONS

Bergmeyer, H. V.; "Methods of Enzymatic Analysis"; Academic Press Inc., vol. 2; pp. 831–855 (1976).
Wilkinson, J. H.; "The Principles and Practice of Diagnostic Enzymology"; Year Book Med. Pub. Inc.; pp. 120–128 (1979).

Primary Examiner—Benoît Castel
Attorney, Agent, or Firm—Oblon, Fisher, Spivak, McClelland & Maier

[57]  ABSTRACT

A rapid, semi-automated method for determining dibucaine numbers is disclosed wherein use is made of a unit dosage form of dibucaine or a test pack containing dibucaine in a unit dosage form.

2 Claims, 2 Drawing Figures

RAPID, SEMI-AUTOMATED METHOD FOR DETERMINING DIBUCAINE NUMBERS

BACKGROUND OF THE INVENTION

1. Field of the Invention

This invention relates to methods for the determination of the Dibucaine Number (DN) and compositions used in said determination.

2. Description of the Prior Art

Approximately one out of 2,500 persons in a normal population has a genetically determined atypical variant of the enzyme: plasma cholinesterase (PchE, E.C.3.1.1.8.). The enzyme has no known physiological role so this variation is of no consequence in our daily lives. However, the enzyme is responsible for the metabolism of the short-acting muscle relaxant, succinylcholine, a drug used daily by anesthesiologists in over 50% of patients to facilitate intubation of the trachea during the conduct of general anesthesia. In the patient with genetically normal PchE, the duration of complete muscle paralysis from succinylcholine is approximately five to seven minutes; however, in those with atypical enzyme, complete paralysis can persist for several hours. These few patients require mechanical ventilation to sustain life until the drug has been eliminated by non-enzymatic pathways.

The assays for PchE will not distinguish the normal enzyme from the atypical variant. However, the normal can be distinguished from the atypical by assaying PchE activity in the presence and absence of dibucaine (a local anesthetic that also inhibits PchE activity). As shown by Kalow and Genest, a given concentration of dibucaine inhibits the activity of the normal enzyme about 80 percent and the atypical about 20 percent.

The dibucaine number determination, Kalow et al. ("A Method for the Detection of Atypical Forms of Human Serum Cholinesterase. Determination of Dibucaine Numbers.", *Can. J. Biochem. Physiol.* 35: 339–346 (1957)) has become the classical method for distinguishing genetically normal plasma cholinesterase from an abnormal variant. This determination is of importance to anesthesiologists because it permits prediction of the response of a specific patient to succinylcholine and it also provides needed information when confronted with post-operative apnea. The dibucaine number is calculated from the ratio of activities of the enzyme with and without DIBUCAINE-HCl ($C_{20}H_{30}ClN_3O_2$) 2-butoxy-N-(2-Diethylaminoethyl)cinchoninamide hydrochloride.

Although the original method of Kalow et al is relatively easy to perform, it is time consuming, it requires advance preparation before samples can be assayed, it requires special skills on the part of the technician and, consequently, results do not usually become available until days or weeks after the information is requested. In most cases, the laboratory performing the assay is geographically separated from the requesting physician.

A need therefore, continues to exist for a rapid, simple, semi-automated method for the determination of dibucaine numbers.

SUMMARY OF THE INVENTION

Accordingly, one object of the invention is to provide a rapid, semi-automated determination of dibucaine number.

A further object of the invention is to provide analytical compositions which allow the use of existing semi-automatic equipment for the determination of plasma cholinesterase activity.

Briefly, these objects and oher objects of the invention as hereinafter will become more readily apparent, can be attained by providing dibucaine in a unit dosage form whereby the preparation of serum samples for analysis of plasma cholinesterase activity using existing laboratory equipment can be attained.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
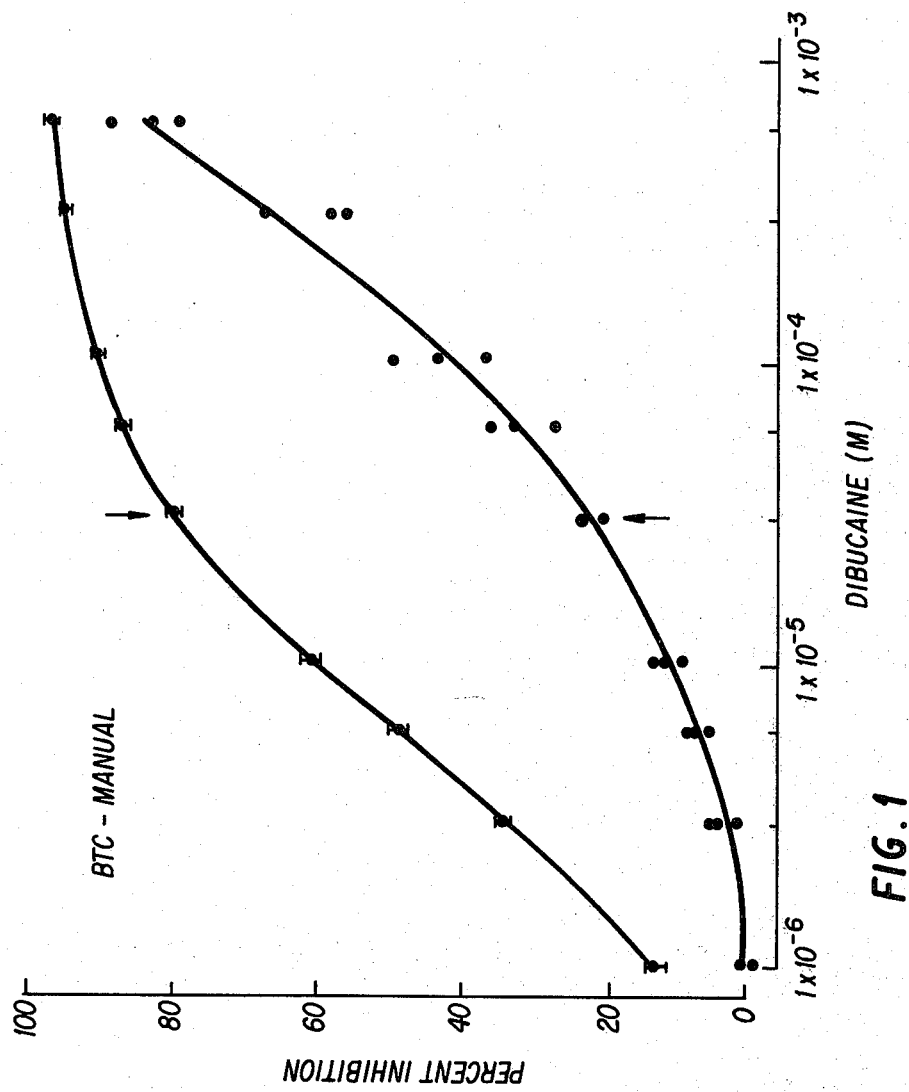
FIG. 1 is a graph showing the inhibition response of normal sera as compared to abnormal sera determined by a manual assay using butyrylthiochline as substrate.

The dibucaine number is used as a basis for differentiating genetically normal plasma cholinesterase from an abnormal variant. This test is based on the fact that dibucaine (within certain concentration limits dependent on the particular substrate used to assay esterase activity) will differentially inhibit the esterase activity of the genetically abnormal variant as compared to the genetically normal plasma cholinesterase. The degree of inhibition, expressed as a percentage, has been termed the "Dibucaine Number", which is reported as:

$$DN = \left[ 1 - \frac{\text{inhibited activity}}{\text{uninhibited activity}} \right] \times 100$$

The classical technique, developed by Kalow et al, was based on the effect of dibucaine inhibiting the esterase activity of serum cholinesterase as measured by the hydrolysis of benzoylcholine (BeCh). Hydrolysis of benzoylcholine being measured by ultraviolet spectrophotometry, the decrease in absorbance at 240 nm (nanometers) being proportional to the hydrolysis of benzoylcholine. At a $1 \times 10^{-5}$ M concentration of dibucaine, the normal esterase was inhibited by about 79%, the abnormal variant by about 17%. Thus, a clear distinction between the two esterases was afforded. However, as previously noted, this method is time consuming, requires advance preparation before samples can be assayed, requires special skills on the part of the technician and results are generally available days or weeks after the information is requested.

Applicant has now discovered a method for an automated determination of the dibucaine number. In contrast to the original method, the automated method consumes minimal time, requires essentially no advance preparation, requires no special technical skills, results become available in one-half to one hour and, in many cases, the assay can be done in the hospital of the requesting physician.

Applicant has developed a method to use existing automated assays for plasma cholinesterase activity to determine the inhibition of plasma cholinesterase activity with dibucaine. Examplary of the equipment available for such automated assays is the DuPont Automatic Clinical Analyzer (DuPont Co., Instrument Products, Automatic Clinical Analysis Division, Wilmington, Del.). This instrument is in widespread use and provides over 30 laboratory determinations of clinical relevance. In particular, an assay for plasma cholinesterase is available with this equipment. The automated technique uses the coupled oxidation-reduction indicator reaction described by Gal et al. (Clin. Chem., Acta, 2, p. 316 (1957)). In this assay butyrylthiochline (BTC) is hydrolyzed by plasma cholinesterace (PCHE) releasing thiocholine which directly reduces the blue dye, 2,6-dichlorophenolindophenol (DIP) to the colorless form.

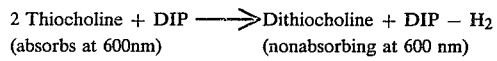

The change in absorbance at 600 nm due to the disappearance of DIP over a 17.07 second measurement period is directly proportional to the PCHE activity, since the reactants are present in non-rate limiting quantities. The operational procedures are exceptionally simple, the operator merely filling a sample cup with sufficient sample, places the sample in an input tray along with a test pack for PCHE and starts the machine. The machine automatically aspirates 0.020 ml of the sample along with 4.980 ml of a phosphate buffer into the test pack for PCHE, which contains ingredients for the assay, i.e., DIP and BTC. The test pack essentially consists of a container holding $0.51\mu$ mol of 2,6-dichlorophenolindophenol as a tablet (combined with excipients) and $10\mu$ mol of butyrylthiocholine as a tablet (combined with excipients). Precise filling of the sample cup is not necessary, as long as sufficient material to constitute the 0.020 ml sample size and the 0.120 ml "dead volume" of the sample cup is used.

Applicant has found that this existing assay may be converted to the determination of dibucaine number by the technique of using the serum sample to reconstitute a solution of a known amount of dry dibucaine. In particular, dibucaine may be prepared in a unit dosage form and this unit dosage reconstituted by a known volume of serum. In one embodiment of this invention, this unit dosage form is a tablet containing a known amount of dry dibucaine and an excipient. Any excipient known to the art may be used, so long as it remains inert to the assay conditions. In a particularly preferred embodiment, a unit dosage device is formed by depositing a predetermined volume of an aqueous solution containing a known amount of dibucaine in a receptacle for a serum sample and lyophilizing the solution to produce a serum sample receptacle coated with a known amount of dibucaine. The serum sample receptacle may be a glass tube. As will become more readily apparent hereinafter, the preferable concentration of dibucaine in the analysis mixture is $1 \times 10^{-4}$ M. In this instance, if $500\mu$ liter serum samples are used, a tube coated with $12.5\mu$ mole of dibucaine is used. This assures a concenration of $1 \times 10^{-4}$ M is the analysis mixture, the serum sample reconstituting the dibucaine into solution. For larger or smaller serum volumes, the unit dosage can be varied to produce a concentration of $1 \times 10^{-4}$ M dibucaine in the analysis mixture. Different concentrations of dibucaine in the analysis mixture may be obtained by variations in the quantity of dibucaine present in the unit dosage tablet or the coating on the receptacle, taking into account the serum sample size and the known 0.020 ml sampling size of the Automatic Clinical Analyzer. Alternatively, the Automatic Clinical Analyzer PCHE test pack may be modified by the addition of a third tablet comprising a pre-determined amount of dibucaine plus excipients. Preferably, the tablet contains $0.5\mu$ mol dibucaine so as to yield the preferred $1 \times 10^{-4}$ M concentration of dibucaine in the analysis mixture (0.020 ml of serum sample and 4.980 ml of phosphate buffer).

Dibucaine number is determined by analysis of two serum samples, one using the standard PCHE assay available with the Automatic Clinical Analyzer (uninhibited activity) and one using the standard PCHE assay wherein the serum sample has been prepared with dibucaine by the above-noted procedure, or the modified PCHE assay test pack.

Having generally described this invention, a further understanding can be obtained by reference to certain specific examples which are provided herein for purposes of illustration only and are not intended to be limiting unless otherwise specified.

Blood samples were obtained by venipuncture. After clot retraction at room temperature, samples were centrifuged and serum was removed for assay or was stored at −20° C. for assay at a later date.

EXAMPLE 1

Each sample was assayed by the method of Kalow et al. Assays were carried out at 25° C. in the presence $(1 \times 10^{-5}$ M) and absence of dibucaine on serum samples diluted 100-fold. The reaction mixture for the two assays is shown in Table I. Dibucaine numbers were calculated by the formula shown at the bottom of Table I.

TABLE I

| | DIBUCAINE NUMBER BENZOYLCHOLINE (BeCh) | |
|---|---|---|
| | Control | Inhibited |
| Serum | + | + |
| Phosphate Buffer 67 mM ph 7.4 | + | + |
| BeCh 5 × 10<sup>−5</sup>M | + | + |
| Dibucaine 1 × 10<sup>−5</sup>M | − | + |

$$DN = \left(1 - \frac{\text{inhibited}}{\text{uninhibited}}\right) \times 100$$

The Kalow et al. technique uses a dibucaine concentration of $1 \times 10^{-5}$ M to distinguish the normal from the abnormal enzyme, based on the original study indicating a dibucaine number of about 80 for the normal enzyme and about 20 for the dibucaine-resistant, or succinylcholine sensitive, variant at this concentration.

The results of the assays on 11 patients with normal plasma cholinesterase and 3 with abnormal sera are tabulated in Table IV.

EXAMPLE II

Serum samples were assayed manually for plasma cholinesterase activity using the method of Ellman et al. ("A New and Rapid Colorimetric Determination of Acetylcholinesterase Activity", *Biochem Pharmacol.* 7: 88–95 (1961)) as modified by Klingman et al. ("Acetyl and Pseudocholinesterase Activities in Sympathetic Ganglia of Rats", *J. Neurochem.* 15: 1121–1130 (1968)). The reaction mixtures are shown in Table II.

TABLE II

| DIBUCAINE NUMBER BUTYRYLTHIOCHOLINE (BTC) - MANUAL | | |
|---|---|---|
| | Control | Inhibited |
| Serum | + | + |
| Phosphate Buffer 100 mM pH 8 | + | + |
| DTNB (indicator) | + | + |
| Dibucaine $1 \times 10^{-6}$M to $6 \times 10^{-4}$M | − | + |
| Neostigmine $2.4 \times 10^{-4}$M | + | + |

The assay differs from the original method of Kalow et al. in that it uses butrylthiocholine, instead of benzoylcholine, as the substrate. Samples were assayed in the presence (concentrations ranging from $1 \times 10^{-6}$ M to $6 \times 10^{-4}$ M) and absence of dibucaine. All reactions were run in duplicate at 37° C.; were linear for at least 10 minutes; and were terminated with neostigmine. Plasma cholinesterase activities were calculated from the increase in optical density of the reaction mixture at 412 nm, resulting from the reaction between thiocholine, this is formed enzymatically from hydrolysis of the substrate, and DTNB, a thiol indicator. The inhibitory effect of dibucaine was calculated from the ratio activities with and without dibucaine.

FIG. 1 shows a plot of the inhibition response of normal sera as compared to abnormal sera obtained in this example. The upper curve is the inhibition response of normal plasma cholinesterase from 11 patients to increasing concentrations of dibucaine. The lower curve is the same response as determined with three abnormal sera. The data show that the inhibition of plasma cholinesterase activity can also be detected by substituting butyrylthiocholine for its classical counterpart:benzoylcholine. As shown by the arrows, at a dibucaine concentration of $3 \times 10^{-5}$ M, the plasma cholinesterase activity of normal serum was inhibited about 80 percent while the activity of the abnormal serum was inhibited about 21 percent. The results establish that a manual assay that closely approximates the assay performed on the Automatic Clinical Analyzer could be used to differentiate normal from abnormal plasma cholinesterase.

The results of the assays on 11 patients with normal plasma cholinesterase and 3 with abnormal sera are tabulated in Table IV.

EXAMPLE III

Serum samples were assayed by modification of the existing automated assay for plasma cholinesterase performed by the DuPont Automatic Clinical Analyzer. The reaction mixtures are shown in Table III.

TABLE III

| BUTYRYLTHIOCHOLINE (BTC) - AUTOMATED | | |
|---|---|---|
| | Control | Inhibited |
| Serum | + | + |
| Phosphate Buffer | + | + |
| BTC | + | + |
| DIP (indicator) | + | + |
| Dibucaine $1 \times 10^{-5}$M to $2 \times 10^{-4}$M | − | + |

The principle of the assay is essentially identical to the manual assay shown in Example 2. The differences are: a different compound for detecting thiocholine, 2,6-dichlorophenolindophenol (DIP); the rapidity of the assay (about 8 minutes per sample); and the lack of need for advance preparation other than the routine maintenance of the instrument. The modification of the existing assay was that some serum samples were assayed with dibucaine at concentrations ranging from $1 \times 10^{-5}$ M to $2 \times 10^{-4}$ M. The desired dibucaine concentrations were achieved by using serum to reconstitute known amounts of dry dibucaine in glass tubes before adding the serum to the autoanalyzer. The dibucaine in these tubes had been added earlier as an aqueous solution and then lyophilized to dryness. The calculated amount of dry dibucaine was confirmed with gas chromatography. The inhibitory effect of dibucaine was calculated from the ratio of activities with and without dibucaine.

Figure 2:
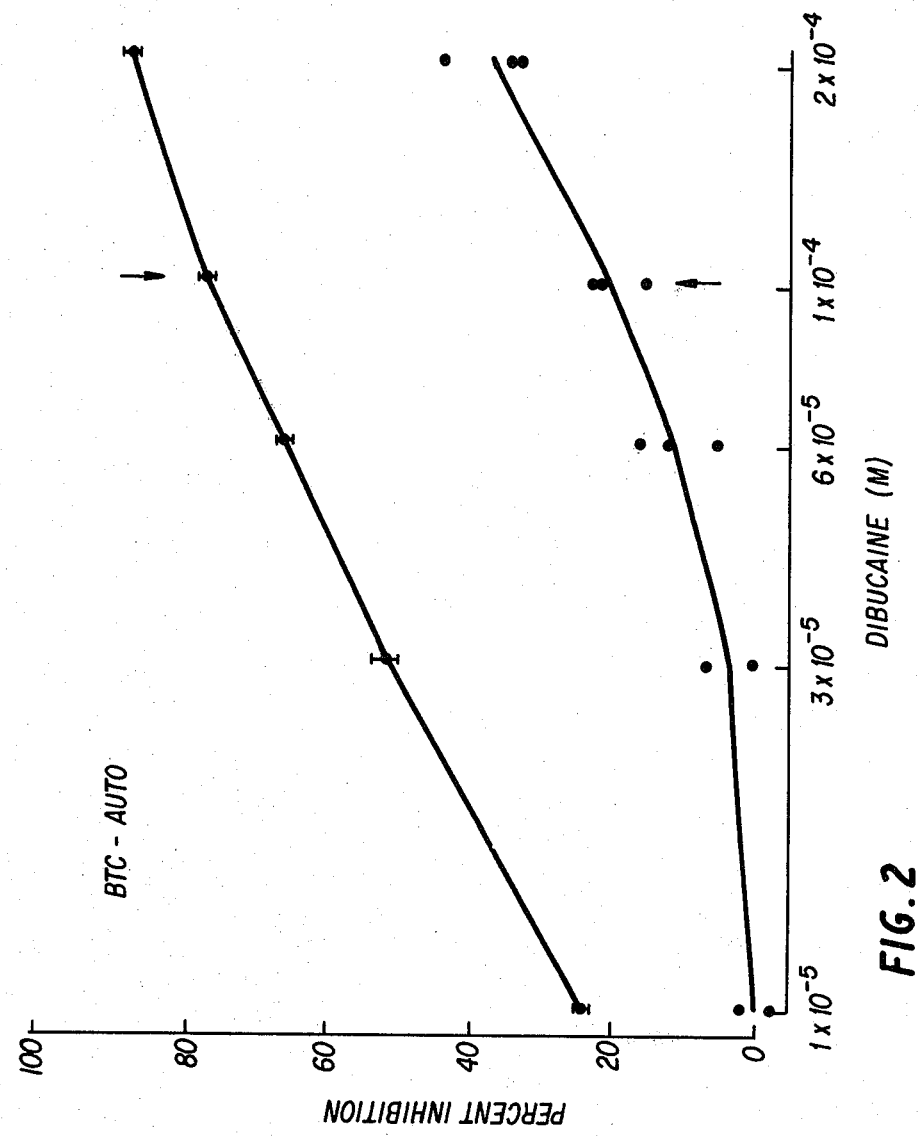
FIG. 2 is a graph showing the inhibition response of normal sera as compared to abnormal sera determined by an automatic assay using butyrylthiocholine as substrate.

FIG. 2 shows a plot of the inhibition response of normal sera as compared to abnormal sera obtained in this Example. The figure shows that plasma cholinesterase activity with the Automatic Clinical Analyzer was also inhibited by dibucaine in a dose-dependent manner. The upper curve is the inhibition response of normal plasma cholinesterase, and the lower curve is the response of the abnormal enzyme. The data shows that the automated assay can differentiate the normal enzyme from the dibucaine resistant variant. At a dibucaine concentration of $1 \times 10^{-4}$ M, as shown by the arrows, the inhibition in 11 normal sera was about 78 percent and in three abnormal sera ranged from 16 to 23 with a mean of 21 percent. This concentration was selected for the determination of dibucaine numbers by the automated assay.

The results of the assays on 11 patients with normal plasma cholinesterase and 3 with abnormal sera are tabulated in Table IV.

TABLE IV

| | DIBUCAINE NUMBER | | |
|---|---|---|---|
| | Benzoylcholine | Butyrylthiocholine | |
| Serum | Manual | Manual | Automated |
| Normal (n = 11) | 74.8 ± 2.9 | 80.0 ± 1.7 | 77.6 ± 1.1 |
| Abnormal #1 | 15.3 | 22.9 | 22.8 |
| #2 | 19.2 | 20.0 | 16.4 |
| #3 | 23.2 | 20.3 | 23.3 |

Table IV is a summary of normal and abnormal dibucaine numbers as determined by the three assay methods described above. Results in the left column were determined by the method of Kalow et al; results in the middle column by the manual method using butrylthiocholine as substrate; and results in the right column by the automated method with the same substrate. As is shown, the two methods using butyrylthiocholine as substrate both result in dibucaine numbers that closely approximate those determined by the classical method. Further, the data show that the automated method can serve as an effective alternative to the classical, more cumbersome method.

Having now fully described this invention, it will be apparent to one of ordinary skill in the art that many changes and modifications can be made thereto without departing from the spirit or scope of the invention set forth herein.

What is claimed as new and desired to be secured by Letters Patent of the United States is:

1. In a method for the determination of dibucaine number by determining the plasma cholinesterase activity of serum samples with and without, dibucaine present, said plasma cholinesterase activity being measured by the hydrolysis of butyrylthiocholine by said serum sample in the presence of the blue dye 2,6-dichlorophenolindophenol, said butyrylthiocholine upon hydrolysis releasing thiocholine which directly reduces the blue dye to a colorless form, the change in absorbance at 600 nm due to the disappearance of 2,6-dichlorophenolindophenol being directly proportional to said plasma cholinesterase activity wherein said activity is measured in the presence of dibucaine to give a value for the inhibited activity and in the absence of dibucaine to give a value for the uninhibited activity and the dibucaine number (DN) is determined by the formula $DN = (1-(\text{inhibited activity}/\text{uninhibited activity})) \times 100$ the improvement comprising preparing serum samples with dibucaine present by using the serum to reconstitute lyophilized dibucaine coated on the walls of a serum sample vessel or present in a tablet in an amount which will yield a concentration of $1 \times 10^{-4}$ M dibucaine in the serum sample.

2. A test pack for the determination of plasma cholinesterase activity in the presence of dibucaine comprising dibucaine, 2,6-dichlorophenolindosphenol and butyrylthiocholine wherein each of the dibucaine, 2,6-dichlorophenolindophenol and butyrylthiocholine is present in an amount of $0.5\mu$ mol, $0.51\mu$ mol and $10\mu$ mol, respectively, and each of the dibucaine, 2,6-dichlorophenolindophenol and butyrylthiocholine is present as an individual tablet containing an excipient.

* * * * *